United States Patent
Hoftman et al.

[11] Patent Number: 5,772,316
[45] Date of Patent: *Jun. 30, 1998

[54] LIGHT HANDLE ADAPTER

[75] Inventors: Mike M. Hoftman, Calabasas; Eli Marmur, Los Angeles, both of Calif.

[73] Assignee: DeRoyal Industries, Inc., Powell, Tenn.

[ * ] Notice: The term of this patent shall not extend beyond the expiration date of Pat. No. 5,599,093.

[21] Appl. No.: 662,702

[22] Filed: Jun. 3, 1996

Related U.S. Application Data

[63] Continuation of Ser. No. 320,007, Oct. 7, 1994, Pat. No. 5,599,093, which is a continuation of Ser. No. 963,200, Oct. 19, 1992, Pat. No. 5,355,292, and a continuation-in-part of Ser. No. 843,144, Feb. 28, 1992, Pat. No. 5,156,456.

[51] Int. Cl.$^6$ .................................................. F21L 15/12
[52] U.S. Cl. ........................ 362/400; 362/804; 16/114 R
[58] Field of Search .............................. 362/33, 399, 400, 362/419, 804; 150/154, 155, 165; 16/111 R, 110 R, 144 R, DIG. 24, DIG. 25

[56] References Cited

U.S. PATENT DOCUMENTS

| | | | |
|---|---|---|---|
| 4,608,124 | 8/1986 | Sandel et al. | 362/804 X |
| 5,036,446 | 7/1991 | Quintanilla et al. | 362/804 X |
| 5,599,093 | 2/1997 | Hoftman et al. | 362/804 X |

Primary Examiner—Stephen F. Husar
Attorney, Agent, or Firm—Loeb & Loeb LLP

[57] ABSTRACT

An assembly for attachment to a conventional operating room light fixture includes a handle and a disposable cover. The handle has an upper portion adapted to be attached to the light fixture. The handle further includes an annular rigid disk at a central portion thereof and an annular ring provided below the annular rigid handle flange and defining a groove therebetween. A grip portion is provided at a lower portion of the handle. The assembly also includes a sterile, disposable cover, including a hollow grip cover having a closed end and a flexible flange formed integrally with the grip cover at an open end thereof and adapted to be fitted over the grip portion of the handle and advanced thereon. The disposable cover further includes a circular rigid cover flange attached to the flexible flange and curved away from the rigid disk when the grip cover is fitted over the grip portion of the handle, with the rigid disk restraining further advancement of the rigid cover flange. The rigid cover flange also includes an opening corresponding to the open end of the grip cover, and a plurality of snaps provided along the circumference of the opening and adapted to be fitted within the groove to securely fit the disposable cover over the handle. For industry-standard handles available with some operating room light fixtures, a light handle adapter may be attached to the standard handle to secure the disposable cover onto the handle. The light handle adapter is slid up the handle toward the light fixture. The light handle adapter may be affixed to the light handle by an adhesive or other mechanical means, and the disposable cover is secured to the light handle adapter.

3 Claims, 4 Drawing Sheets

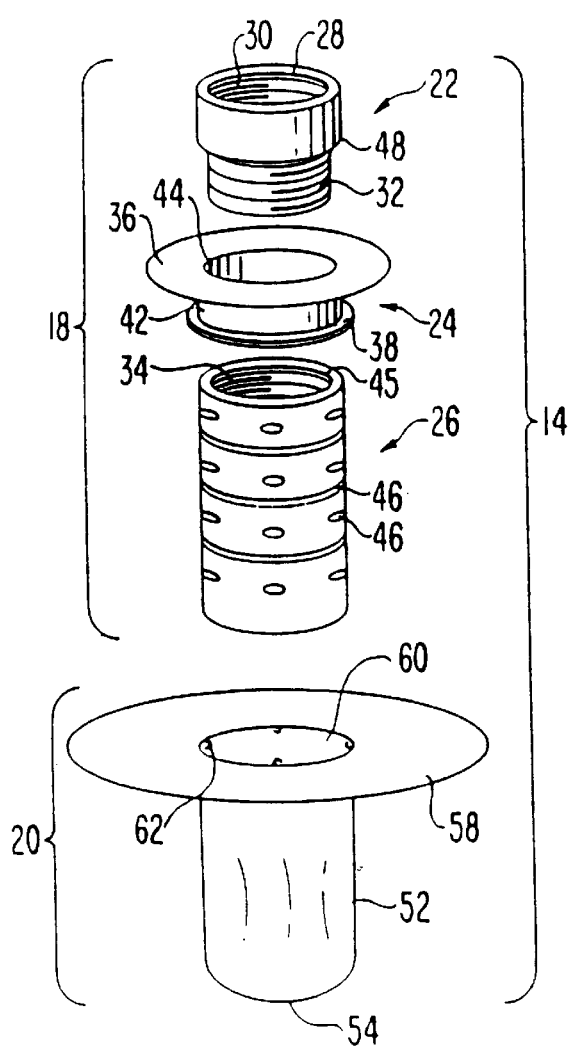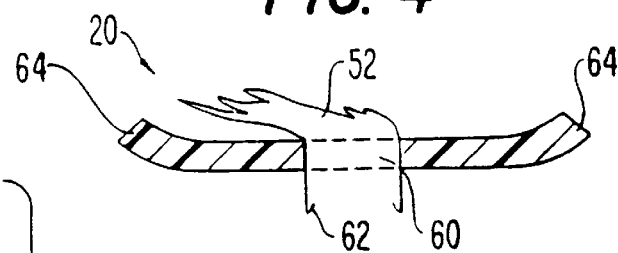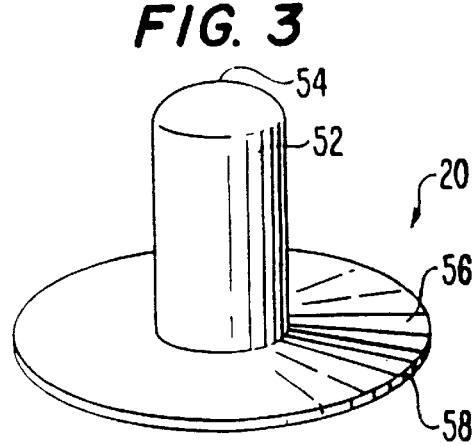

LIGHT HANDLE ADAPTER

This is a continuation of application Ser. No. 08/320,007 filed on Oct. 7, 1994, now U.S. Pat. 5,599,093 which is a continuation of application Ser. No. 07/963,200, filed on Oct. 19, 1992, now U.S. Pat. No. 5,355,292, and a continuation-in-part of application Ser. No. 07/843,144, filed on Feb. 28, 1992, now U.S. Pat. No. 5,156,456.

BACKGROUND OF THE INVENTION

The present invention relates in general to hospital surgery room equipment and specifically to a replacement handle for a surgical room light fixture and a disposable cover for use with the replacement handle.

DESCRIPTION OF THE RELATED ART

A sterile environment must be established and maintained in an operating room. Everything which is in the operating room sterile field must be sterilized. Certain reusable items are sterilized after each use, which may be very expensive and troublesome. As a result, it is frequently more economical to use disposable sterile items as opposed to sterilizing reusable items.

Unfortunately, it is neither practical nor economical to dispose of large operating room fixtures, such as lighting fixtures, after each operation. Since any item which is touched by any person who enters the sterile field of an operating room must be sterilized, there must be a way of maintaining the sterility of such large fixtures. Alternatively, steps must be taken to prevent surgical personnel from contacting non-sterile portions of such fixtures that are outside the sterile field of an operating room.

Operating room light fixtures are provided with reusable handles for use by surgical personnel to adjust the angle of incidence upon the operating areas or to bring the light closer to the area which is being operated on during surgery. The lighting fixture handle is normally situated in the middle of the light housing and depends therefrom. Since the handle is being constantly manipulated by surgical personnel during surgery, it must be maintained sterile. Surgical personnel must also be prevented from contacting other portions of the lighting fixture other than the sterile handle. These other portions are non-sterile and are not likely to be sterilized because they are outside the sterile field of an operation. There are currently a number of attempts to address these problems.

First, removable handles of operating room light fixtures are provided so that, in between operations, the handles may be removed and sterilized prior to the next operation. However, this is particularly disadvantageous because it requires very expensive personnel time to remove, clean and sterilize the equipment, expensive materials to wrap it, and sterilization itself could also be troublesome and costly.

Second, sterile disposable handles are provided and are then disposed of after each operation. Examples of such disposable handles are disclosed in U.S. Pat. Nos. 4,844,252 to Barron et al. and 4,974,288 to Reasner. However, it is rather expensive to replace sets of operating room light fixture handles after each operation, which will increase the cost of the operation to the patient. Further, these handles are bulky, requiring more storage space, which is limited at hospitals, and create more waste to the environment. Also, removal of the bloody, "contaminated" handles exposes hospital personnel to the contaminated surfaces.

Third, due to the high cost of the above two alternatives, sterile disposable covers have been provided for covering an operating room light fixture handle. Examples of such sterile disposable covers are disclosed in U.S. Pat. Nos. 4,605,124 to Sandel et al. and 4,976,299 to Bickelman. However, each of these disposable covers suffers from some drawbacks.

More particularly, U.S. Pat. No. 4,605,124 discloses a disposable cover 18 having a cylindrical grip 24 and integral flange 28, and shaped in a manner to surround and fit the corresponding portion 29 of the handle 20. The flange 28 may either be flat-shaped or bell-shaped, depending on the corresponding shape of the handle. Adhesive can be applied to the interior portions of the flange 28 in order to firmly attach the cover 18 to the handle 20. This patent also discloses an adapter kit for adapting the handle cover for use with the light fixture. The adapter kit comprises an internally and externally threaded bushing 234 and an internally threaded adapter handle 220. The bushing 234 is threaded on its inside to attach to a mating threaded bolt extending from the light fixture. The bushing 234 also has outside threads which are used to attach the bushing 234 to the adapter handle 220.

The disposable cover disclosed in U.S. Pat. No. 4,605,124 suffers from several drawbacks. First, since the flange 28 is flexible and is adapted to the shape of the handle 20, the disposable cover does not have a protective guard which prevents the nurse's or surgeon's hand from sliding past the flange portion 28 and contacting non-sterile portions of the surgical room light fixture. Second, the use of adhesive to firmly attach the cover 18 to the handle 20 is troublesome. Third, due to the flexibility of the flange 28, the nurse's or surgeon's glove may become contaminated while applying the cover to the light handle. Fourth, the cover itself may become contaminated from prior folds while it is being applied over the light handle if the cover edge contacts the non-sterile light handle flange.

U.S. Pat. No. 4,976,299 discloses a sterile disposable cover 11 having a cylindrical hollow member 12 and a guard 13. The guard 13 acts to prevent a surgeon's hand from contacting non-sterile portions of a light fixture. The cover 11 also includes a retention number 17 which partially closes the opening of an opened end 15. The retention number 17 may be a circular plastic disk which is adhered within an annular recessed portion 18 in the guard 13. However, referring to FIG. 1 of this patent, the disposable cover 11 of this patent suffers from the drawback that the guard 13 does not appear to be sufficiently rigid and is adapted to the shape of the handle and/or light fixture. Thus, it is possible that the surgeon's hand may slide past the guard 13 and contact non-sterile portions of the light fixture. In addition, the retention disk 17 inhibits the application of the cover to the corresponding handle, as well as the removal of the cover. It also inhibits the application of a second cover over the first one if necessary in case of accidental contamination during the surgical procedure.

SUMMARY OF THE DISCLOSURE

In order to accomplish the objects of the present invention, an assembly including a handle and a disposable cover is provided for attachment to a conventional operation room light fixture. The handle includes an adapter having an upper portion adapted to be attached to the light fixture, and a lower portion coupled to a grip portion at an upper portion thereof. A central ring-shaped stud is provided between the adapter and the grip portion, and has an annular rigid disk and an annular ring provided below the annular rigid disk to define a groove therebetween. The stud has a channel which allows the lower portion of the adapter to pass therethrough to engage the grip portion.

The assembly according to embodiments of the present invention also includes a sterile, disposable cover, including a hollow grip cover having a closed end and a flexible flange formed integrally with the grip cover at an open end thereof. The disposable cover further includes a circular rigid cover flange attached to the flexible flange, the rigid cover flange curved towards the grip cover and including an opening corresponding to the open end of the grip cover, and a plurality of snaps provided along the circumference of the opening. The grip cover may be fitted over the grip portion of the handle and advanced thereon so that the rigid cover flange curves away from the handle rigid disk, with the rigid disk restraining further advancement of the rigid cover flange, and the snaps may be fitted within the groove to securely fit the disposable cover over the handle.

The combined surgical light fixture handle and disposable cover according to embodiments of the present invention provides an economical and simple means for maintaining the sterility of an operating room light fixture handle, and for preventing a surgeon from contacting non-sterile portions of the light fixture while applying the cover to the handle or during the manipulation of the light during surgery. Furthermore, this cover cannot become contaminated during its application to the handle. A second cover can be applied over the first cover to maintain sterility of the light handle if the first cover becomes inadvertently contaminated. The easy application of the second cover minimizes unnecessary delays during surgical procedures.

The handle of the present invention has only a few basic components, is simple in construction and is easy to manufacture. The one-piece construction of the disposable cover of the present invention is also simple and easy to manufacture. This cover may also be collapsed for reduced sterilization costs, easy packaging, storage, transportation, and disposal. The locking mechanism which interacts between the handle and cover of the present invention allows the disposable cover to be firmly secured to the handle while preventing the surgeon's hand from contacting any non-sterile portions of the light fixture. The curvature of the rigid cover flange induces a surgeon's hand to slide towards the center of the cover and away from non-sterile portions of the light fixture.

If standard, conventional light handles are already in place or incorporated into the light fixture, an adapter may be attached to the light handle so that the disposable cover may be easily fitted over the reusable handle and secured in place without requiring that the handle itself be replaced.

BRIEF DESCRIPTION OF THE DRAWINGS

Further objects, advantages and features of the invention will become apparent from the detailed description of the preferred embodiments when read in conjunction with the accompanying drawings, in which:

FIG. 2 is an exploded perspective view of the handle and disposable cover of the present invention.

FIG. 3 is a perspective view of the disposable cover of FIG. 2.

FIG. 4 is a cross-sectional view of the disposable cover of FIG. 2 in a collapsed orientation.

DETAILED DESCRIPTION OF THE PREFERRED EMBODIMENTS

The following detailed description is of the best presently contemplated mode of carrying out the invention. This description is not to be taken in a limiting sense, but is made merely for the purpose of illustrating general principles of embodiments of the invention. The scope of the invention is best defined by the appended claims.

Figure 1:
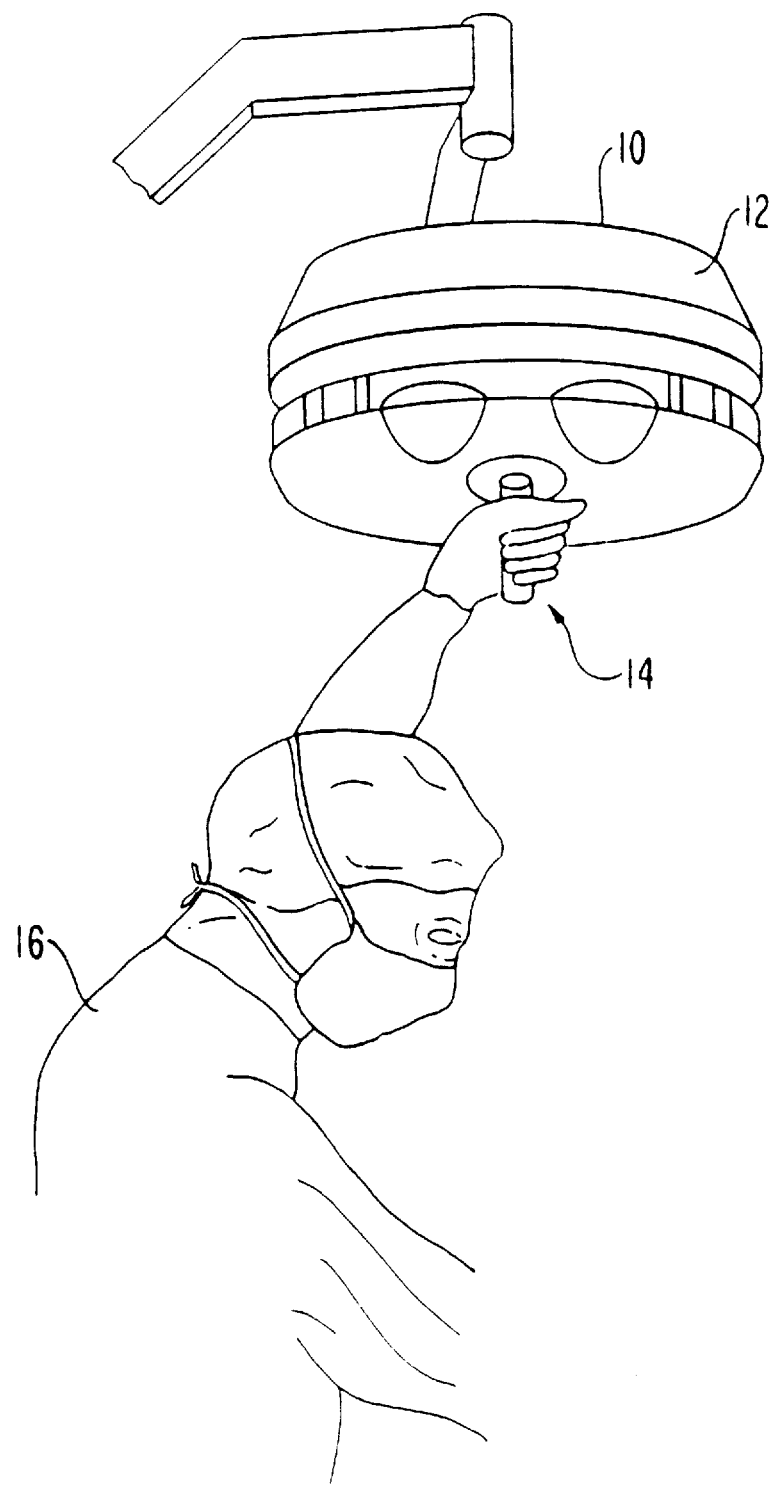
FIG. 1 is a perspective view showing an operating room lighting fixture equipped with an exemplary embodiment of the handle and disposable cover of the present invention.

Referring to FIG. 1, a surgical lighting fixture 10 is comprised of a body 12 and has a manual handle and cover assembly 14 for use by surgical personnel, for example a surgeon designated by 16. The lighting fixture 10 is suspended over the head of the surgeon 16 performing the surgical procedure. The surgeon may make adjustments to the lighting fixture orientation, including the angle of light incidence, during the surgery by manipulating the cover and handle assembly 14.

Referring to FIGS. 2 and 3, the handle and cover assembly 14 is comprised of a replacement handle 18 for a lighting fixture and a sterile disposable cover 20. The handle 18 may be attached to the underside of the light fixture body 12, as shown in FIG. 1, and the sterile disposable cover 20 may be fitted over the handle 18 to ensure the sterility of the handle for manipulation during surgery.

Referring to FIG. 2, the handle 18 is comprised of three primary components, an adapter 22, a central stud 24, and a handle grip portion 26. The adapter 22 has a bore 28 which has internal threads 30 for receiving a large threaded bolt (not shown) from the body 12 of the lighting fixture 10. The adapter 22 also has a lower threaded portion 32 for threadingly engaging the inner threads 34 of the handle grip 26. The stud 24 has an annular rigid disk 36 and an annular ring 38 provided slightly below the annular rigid disk 36, with the space between the annular rigid disk 36 and the annular ring 38 defining a groove 42. The stud 24 is provided with a channel 44 which is adapted for the lower threaded portion 32 of the adapter 22 to pass therethrough. The handle grip portion 26 has a bore 45 which is provided with inner threads 34. The surface of the handle grip portion 26 may be provided with small closely-spaced indentations 46, some spanning across the entire circumference of the grip portion 26, to facilitate a positive grip thereon. It will be fully appreciated by those skilled in the art that the shape, size and configuration of the handle grip portion 26, including its surface, may be varied without departing from the spirit and scope of the present invention.

The handle 18 is assembled by slipping the lower threaded portion 32 of the adapter 22 through the channel 44 until the annular disk 36 abuts against a stop ring 48 located at the uppermost part of the threaded portion 32. At this point, the threads of the threaded portion 32 extend from the bottom of the stud 24. The combined adapter 22 and stud 24 is taken and the lower threaded portion 32 is applied with glue and then rotated to threadingly engage the threads 34 of the bore 45 of the handle grip portion 26. The combined handle 18 is then taken and engaged into the body 12 of the light fixture 10 by turning the threaded upper bore 28 to receive a threaded bolt (not shown) of the light fixture 10.

Referring now to FIGS. 2 and 3, the sterile disposable cover 20 has a flexible, collapsible, thin-walled elastic grip cover 52 with a closed end 54. The grip cover 52 is cylindrical and is formed integrally with a flexible flange 56 which is also made of the same material as the grip cover 52. The flexible flange 56 is attached by, for example, heat sealing or thermal bonding, to a rigid cover flange 58. The rigid cover flange 58 is angled towards the grip cover 52 as shown at 64 in FIG. 4. Since the flexible flange 56 is attached to the rigid cover flange 58, the flexible flange 56 also assumes the angled orientation. The rigid cover flange 58 is provided with a central circular opening 60 which acts as an opening to the opened end of the hollow internal volume of the grip cover 52. Four hook-shaped snaps 62 are provided in spaced-apart fashion around the internal circumference of the opening 60.

Figure 5:
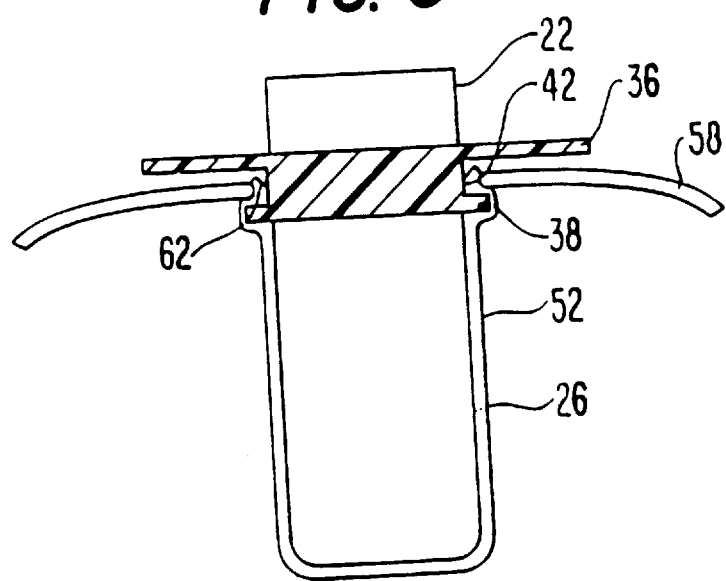
FIG. 5 is a cross-sectional view of the disposable cover of FIG. 2 as used with the light fixture handle of FIG. 2.

In operation, the sterile disposable cover 20 may be used to cover the handle 18 by sliding the hollow grip cover 52 through its opened end over the handle grip portion 26 of the handle 18 (see FIG. 5). The grip cover 52 is slid upwardly until the portion of the rigid cover flange 58 at the opening 60 abuts the annular rigid disk 36 of the handle 18. At this point, the four hook-shaped snaps 62 may be snap-fitted within the groove 42 to secure the grip cover 52 in place over the handle grip portion 26 of the handle 18. The rigidity of the cover flange 58 and its curvature or angling away from the disk 36 prevents a nurse's or surgeon's hand from slipping past the cover flange 58 and contacting non-sterile portions of the light fixture 10. In particular, the curvature of the cover flange 58 induces a nurse's or surgeon's hand to slide towards the center of the cover 20 and away from the non-sterile portions of the light fixture 10. The disk 36 acts as an impediment towards the further advancement of the cover 20, and also provides more stability towards the restraint provided by the cover flange 58.

The cover 20 is formed from a plastic material and then packaged and subsequently sterilized. The material used for the grip cover 52 may be composed of any thin-walled elastic sterilizable material such as plastic, synthetic rubber, silicone, or latex or any other material that will remain impervious even while exposed to any conventional sterilization processes. The material should also have the capability of being stretched and expanded slightly without tearing to fit varying handle sizes within a prescribed range of sizes. The thickness of the grip cover 52 and the flexible flange 56 is about 3–10 mils. The rigid cover flange 58 is made of a rigid plastic material and is approximately 20–50 mils thick. It is fully appreciated by those skilled in the art that any conventional manufacturing process with mechanical or thermal bonding capabilities may be used to attach the flexible flange 56 to the rigid cover flange 58.

It is understood by those skilled in the art that the adapter 22, the stud 24, and the grip portion 26 of the handle 18 may be provided in different shapes and sizes, depending on the preferences and/or requirements of the hospital and/or surgical personnel. The corresponding bore 45 and the threaded lower portion 32 are all made of a standard size to allow one or more of the components to be used interchangeably while retaining the other components. For example, depending upon the hospital and/or the surgical personnel, it may be preferred to have a handle 18 with a wider rigid disk 36. In this situation, the surgeon may prefer the stud 24 with a wider rigid disk 36, while retaining the original adapter 22 and grip portion 26. The components of the handle 18 may be made from anodized aluminum or other light metal or rigid plastic materials.

The cover 20 may be easily packaged and stored by pressing down on the collapsible grip cover 52 so that the grip cover 52 may be folded over and pressed flat against the cover flange 58 as shown in FIG. 4. Thus, the resulting cover 20 takes the circular shape of the cover flange 58, and its simple one-piece construction allows it to be easily placed in a relatively flat package for storage or disposal, without the need for folding. The compactness of the flat packaging used for the cover 20 results in reduced sterilization, packaging, disposal and transportation costs, and in increased savings of space. This also allows the cover 20 to be more customer-friendly.

The handle and cover combination of the present invention provides a stable and secure fit of a sterile disposable cover 20 onto a replacement handle 18 of a surgical light fixture. The rigidity of the cover flange 58 and its curvature away from the handle flange 38 ensure that a surgeon's hands will not slide past the rigid cover flange 58 of the cover 20 and onto nonsterile portions of the lighting fixture 10 while applying it to the handle 18 or during the manipulation of the handle 18. The locking or securing mechanism of the snaps 62 in the groove 42 also ensure that the cover 20 will not fall off easily and can be securely held in place during the duration of the surgery. It should also be understood and appreciated by those skilled in the art that a relatively flat handle flange 38 having little or no curvature can be provided without departing from the spirit and scope of the present invention.

Both the handle 18 and the cover 20 are also simple in construction. Furthermore, the one-piece construction of the cover 20 is easy to manufacture, package, store and dispose.

Figure 7:
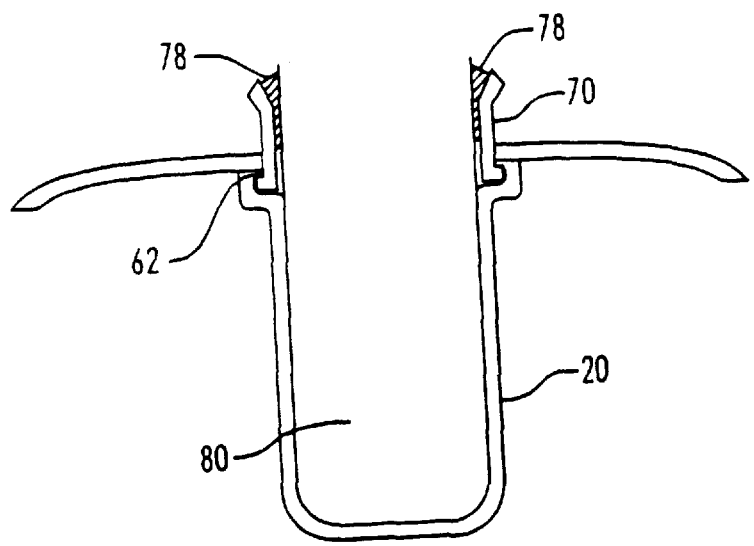
FIG. 7 is a cross-sectional view of the light handle adapter of FIG. 6 as used with a standard light handle and the disposable cover of FIG. 2.
Figure 6:
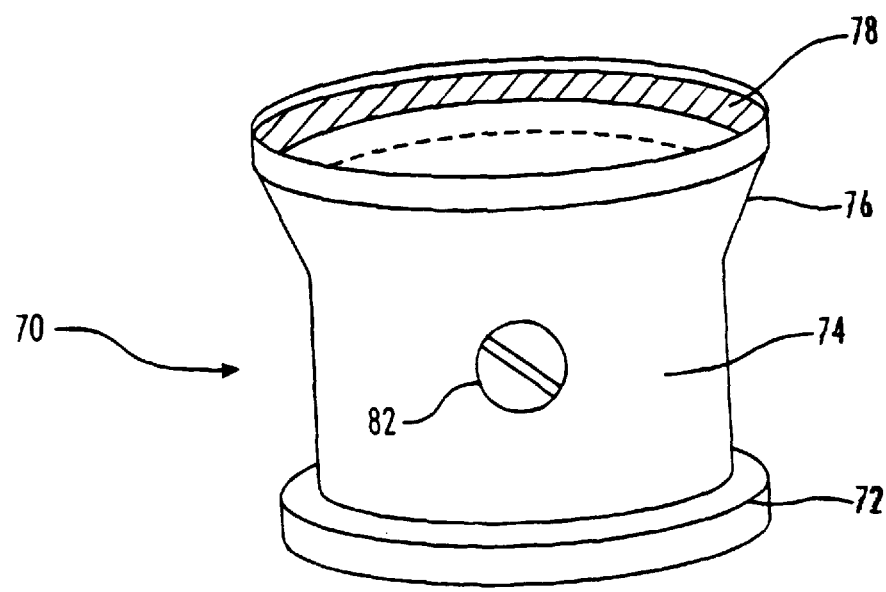
FIG. 6 is a perspective view of a light handle adapter in accordance with one embodiment of the present invention.

In a different embodiment of the present invention, a light handle adapter may be used with an industry-standard light handle that may not be provided with a predefined groove, as in groove 42 of the replacement handle 18 described above. Referring to FIGS. 6 and 7, a light handle adapter 70 forms a cylindrical ring which is adapted to slidably fit over a standard, reusable light handle 80. As shown in FIG. 6, the light handle adapter 70 has an annular ring 72 coupled to one end of a cylindrical body portion 74. The opposite end of the cylindrical body portion 74 extends outwardly into a flared, funnel-shaped flange 76. The flared flange 76 is adapted for slidably receiving the free end of a standard light handle 80, as shown in FIG. 7. The flared flange 76 and cylindrical body 74 structure may be slid toward the lighting fixture.

Depending upon the shape of the light handle 80 as it extends toward the lighting fixture, the slidability of the light handle adapter 70 may be limited by the diameter of the light handle 80 relative to the light handle adapter 70. For example, some standard light handles may become smaller in diameter as they extend from the lighting fixture to the free end of the light handle. Thus, if the light handle adapter 70 of the present described embodiment is selected so that the diameter of the light handle adapter 70 slidably fits over the smaller end of the light handle 80, as the handle adapter 70 is slid up the light handle 80 toward the lighting fixture, the advancement of the light handle adapter may be limited by the increasing diameter of the light handle 80. In another example, the light handle 80 may be configured in the shape of a cylinder having a constant diameter throughout the length of the light handle. In such case, the light handle adapter 70 may be slid up to the point where the length of the light handle 80 itself prevents further movement toward the lighting fixture.

The light handle adapter 70 is affixed to the light handle 80 by means of an adhesive 78, as shown in FIGS. 6 and 7. Various adhesives may be used for securely affixing the light handle adapter to the light handle. Other mechanical means such as a set screw 82 may also be used alone or in conjunction with an adhesive. For example, one side of a double-sided adhesive 78 may be attached to the light handle adapter 70 so that when the light handle adapter 70 is slid into position at a desired location along the length of the handle 80, the opposite side of the adhesive 78 may be affixed to the light handle 80. Preferably, the adhesive does not extend to the cylindrical body portion 74 of the light handle adapter 70, but is affixed on one side only to the flared flange 76. In this way, the adhesive may readily be affixed to the light handle 80, while simultaneously allowing slidable movement of the cylindrical body portion 72 of the light handle adapter 70 along the length of the light handle 80 until the desired position is reached.

As shown in FIG. 7, an annular ring 72 is coupled to the end of the cylindrical body portion 74. As described above with respect to FIG. 5, the sterile disposable cover 20 is used to cover the standard light handle 80 by sliding the hollow grip cover 52 over the light handle 80 until the rigid covered flange 58 at the opening 60 abuts the base of the flared flange 76. The sterile disposable cover 20 is then secured to the light handle adapter 70 by the four hook-shaped snaps 62 which engage the lip formed by the coupling between the cylindrical body portion 74 and the annular ring 72. As discussed above, the rigidity of the cover flange 58 and its curvature or angling away from the flared flange 76 prevents a user's hand from slipping past the cover flange 58 and contacting non-sterile portions of the light fixture or light handle adapter 70. If the disposable cover 20 becomes inadvertently contaminated during a surgical procedure, another cover may be slipped over the one already in place.

If desired, the light handle adapter may be removed from the light handle by prying the adhesive loose and sliding the light handle adapter away from the lighting fixture, off of the light handle 80. Any type of industrial solvent may be used to clean the adhesive from the light handle 80. The light handle adapter will not need to be replaced for reasons of sterility because, when in use, only the sterile disposable cover 20, as shown in FIGS. 2, 3 and 5, will be handled.

The light handle adapter may be made of any rigid material sufficient to secure the hook-shaped snap 62 over the protruding annular ring 72. Various types of adhesives or mechanical means may be used to secure the light handle adapter to the lighting fixture. Preferably, a double-sided adhesive tape which is sufficiently strong is used to securely fasten the light handle adapter 70 to the light handle 80. Adjustment of the lighting fixture by a user grasping the sterile disposable cover will not cause the sterile disposable cover 20 to be removed. After each usage of a new sterile disposable cover 20, the disposable cover 20 may be removed simply by peeling off the cover with the contaminated surface inverted to contain any contaminants. The disposable cover may then be disposed. To prepare for the next usage, a new disposable cover can be slipped over the handle and fastened to the light handle adapter. Furthermore, in case of accidental contamination during surgery, a second cover may be slipped over the first one to avoid any unnecessary delays.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method of maintaining the sterility of an operating room light fixture to be adjusted manually by a user, the method comprising the steps of:

a coupling a handle means to the light fixture, the handle means for controlling the adjustment of the light fixture;

covering the handle means with a first sterile disposable cover, the first sterile disposable cover covering the handle means such that the user contacts only the sterile disposable cover; and covering the first sterile disposable cover with a second sterile disposable cover so that the second sterile disposable cover is not easily removed from the light fixture handle when the light fixture is adjusted by the user.

2. A method of maintaining the sterility of an operating room light fixture to be adjusted manually by a user, the method comprising the steps of:

coupling a handle means to the light fixture, the handle means for controlling the adjustment of the light fixture;

covering the handle means with a flexible sterile disposable cover, the sterile disposable cover having an exterior surface adapted to come in contact with the user's hand; and inverting the exterior surface by peeling the sterile disposable cover off the handle means.

3. A method according to claim 2, wherein the sterile disposable cover has a cylindrical hollow grip cover made from a thin-walled elastic material.

* * * * *

UNITED STATES PATENT AND TRADEMARK OFFICE
CERTIFICATE OF CORRECTION

PATENT NO.   :  5,772,316
DATED        :  June 30, 1998
INVENTOR(S)  :  Mike M. Hoftman It is certified that error appears in the above-indentified patent and that said Letters Patent is hereby corrected as shown below:

TITLE PAGE:

After [75] Inventors: Mike M. Hoftman, Calabasas", delete "; Eli Marmur, Los Angeles, both of Calif.", and insert --, Calif.--.

Signed and Sealed this

Twenty-seventh Day of October, 1998

Attest:

BRUCE LEHMAN

Attesting Officer

Commissioner of Patents and Trademarks